(12) United States Patent
Ott

(10) Patent No.: US 10,195,371 B2
(45) Date of Patent: *Feb. 5, 2019

(54) TROCAR SLEEVE

(71) Applicant: Douglas E Ott, Macon, GA (US)

(72) Inventor: Douglas E Ott, Macon, GA (US)

(73) Assignee: LEXION MEDICAL LLC, St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/731,893

(22) Filed: Jun. 5, 2015

(65) Prior Publication Data

US 2015/0265785 A1    Sep. 24, 2015

Related U.S. Application Data

(63) Continuation of application No. 14/306,562, filed on Jun. 17, 2014, now Pat. No. 9,199,046, and a continuation of application No. 12/658,086, filed on Feb. 2, 2010, now Pat. No. 9,566,401, which is a continuation of application No. 11/058,435, filed on Feb. 15, 2005, now Pat. No. 7,722,558.

(51) Int. Cl.
| | | |
|---|---|---|
| *A61M 5/00* | (2006.01) | |
| *A61M 13/00* | (2006.01) | |
| *A61B 17/34* | (2006.01) | |
| *A61M 3/00* | (2006.01) | |

(52) U.S. Cl.
CPC ....... *A61M 13/003* (2013.01); *A61B 17/3415* (2013.01); *A61B 17/3474* (2013.01); *A61B 17/3496* (2013.01); *A61M 3/00* (2013.01); *A61M 5/00* (2013.01); *A61M 2206/20* (2013.01)

(58) Field of Classification Search
None
See application file for complete search history.

(56) References Cited

U.S. PATENT DOCUMENTS

| | | | |
|---|---|---|---|
| 3,699,962 A | 10/1972 | Hanke | |
| 3,810,471 A * | 5/1974 | Truhan | A61M 1/0084 604/45 |
| 4,294,250 A | 10/1981 | Dennehey | |
| 4,808,168 A | 2/1989 | Warring | |
| 4,869,717 A | 9/1989 | Adair | |
| 5,104,381 A | 4/1992 | Gresl et al. | |
| 5,300,084 A | 4/1994 | Johnson | |
| 5,334,150 A | 8/1994 | Kaali | |
| 5,407,427 A | 4/1995 | Zhu et al. | |
| 5,411,474 A | 5/1995 | Ott et al. | |
| 5,431,676 A | 7/1995 | Dubrul et al. | |
| 5,545,150 A | 8/1996 | Danks et al. | |

(Continued)

OTHER PUBLICATIONS

File History—US9095372

(Continued)

*Primary Examiner* — Michael Carey
*Assistant Examiner* — Elizabeth K So
(74) *Attorney, Agent, or Firm* — Johnson & Phung LLC

(57) ABSTRACT

A trocar sleeve that isolates the surgical device or movement thereof to inhibit or prevent an established non-jet streaming condition from becoming a jet streaming condition and a method of inhibiting or preventing a jet streaming condition from occurring due to instrument obstruction.

18 Claims, 2 Drawing Sheets

(56) References Cited

U.S. PATENT DOCUMENTS

| | | | |
|---|---|---|---|
| 5,605,537 A * | 2/1997 | Ivey | A61B 17/3203 604/21 |
| 5,776,097 A | 7/1998 | Massoud | |
| 5,779,699 A | 7/1998 | Lipson | |
| 5,984,941 A | 11/1999 | Wilson et al. | |
| 6,190,303 B1 | 2/2001 | Glenn et al. | |
| 6,324,812 B1 | 12/2001 | Drya-Lisiecka | |
| 6,504,268 B1 | 1/2003 | Flegel | |
| 6,733,479 B1 * | 5/2004 | Ott | A61B 17/3421 604/158 |
| 6,905,489 B2 | 6/2005 | Mantell et al. | |
| 7,476,212 B2 | 1/2009 | Spearman et al. | |
| 7,722,558 B2 | 5/2010 | Ott | |
| 7,967,788 B2 | 6/2011 | Chandrasekar et al. | |
| 8,111,966 B2 | 2/2012 | Holmberg et al. | |
| 8,439,888 B2 | 5/2013 | Harkness | |
| 8,608,697 B2 | 12/2013 | Tran | |
| 9,095,372 B2 | 8/2015 | Stearns et al. | |
| 2002/0004646 A1 | 1/2002 | Manhes | |
| 2004/0167473 A1 * | 8/2004 | Moenning | A61B 17/3439 604/164.02 |
| 2005/0137529 A1 | 6/2005 | Mantell | |
| 2005/0288551 A1 | 12/2005 | Callister et al. | |
| 2006/0184095 A1 | 8/2006 | Ott et al. | |

OTHER PUBLICATIONS

Declaration at Dubrul.
Dec. 12, 2016 CV for William Dubrul.
Rexam Cert—US5411474.
Complaint in 16-CV-00944 (EDNY).
Handbook of Plastics Joining.
US FDA GFR Title 21.
Webster's 3rd New International Dictionary.
Lexion Exhibit 1020 Drawing.
Modifications of the Closed Technique Article.
Rebuttal Declaraion of William Dubrul.
Deposition of David Lipson, PhD.
US Patent Searcn Results, terms "cooperate" & "cooperating".
American Heritage Dictionary, "cooperate".
FOA-2015-04-10-14298419.
Amendment-2015-05-01-14298419.
Interview-Summary-2015-05-01-14298419.
Interview-Summary-2015-06-08-14298419.
Severe Local Hypothermia from Laparoscopic Evaporative Jet Co....
Jul. 1, 2014 Substitute Specification.
Jun. 7, 2014 Original Specification.
Feb. 12, 2015 Amendment.
Dr. David Lipson Declaration.
Oct. 4, 2017 Dubrul Deposition.
Cambridge Dictionary Definition—Cooperate.
Babylon Dictionary Definition—Cooperate.
David Lipson CV.
Wiley Encyclopedia Excerpts.
Babylon Dictionary Definition—Latch.
Selecting Garment Accessories, Trims and Closures.
Fig. 44 of '372.
Text & drawing (Fig. 45 of '372).
Fig. 45 of '372.
Deposition ot Wiliam Dubrul.
IPR Petition.
Notice of Filing Date.
Patent Owner Notice.
Power of Attorney.
Patent Owner Power of Attorney.
Patent Owner Preliminary Response.
Institution Decision.
Scheduling Order.
Updated Mandatory Notices.
Notice of Deposition of Lipson.
Patent Owners Response.
Surgiquest Notice of subsequent Authority.
Petitioner's Reply to Patent Owner's Response.
Patent Owner's Objections to Evidence.
Notice of Deposition of Dubrul.
Patent Owner's Motion to Substitute Counsel.
Hatent owner's updated Hower of Attorney.
Order Conduct of the Hroceeding.
Order Motion to Subsitute Counsel.
Petitioner's Request for Oral Argument.
Patent Owner's Motion to Strike.
Hatent Owners Request for Oral Argument.
Patent Owner's Motion for Observations.
Order Oral Argument.
Opposition to Motion to Strike.
Petitioner's Response to Motion for Observation.
Power of Attorney—Lexion.

* cited by examiner

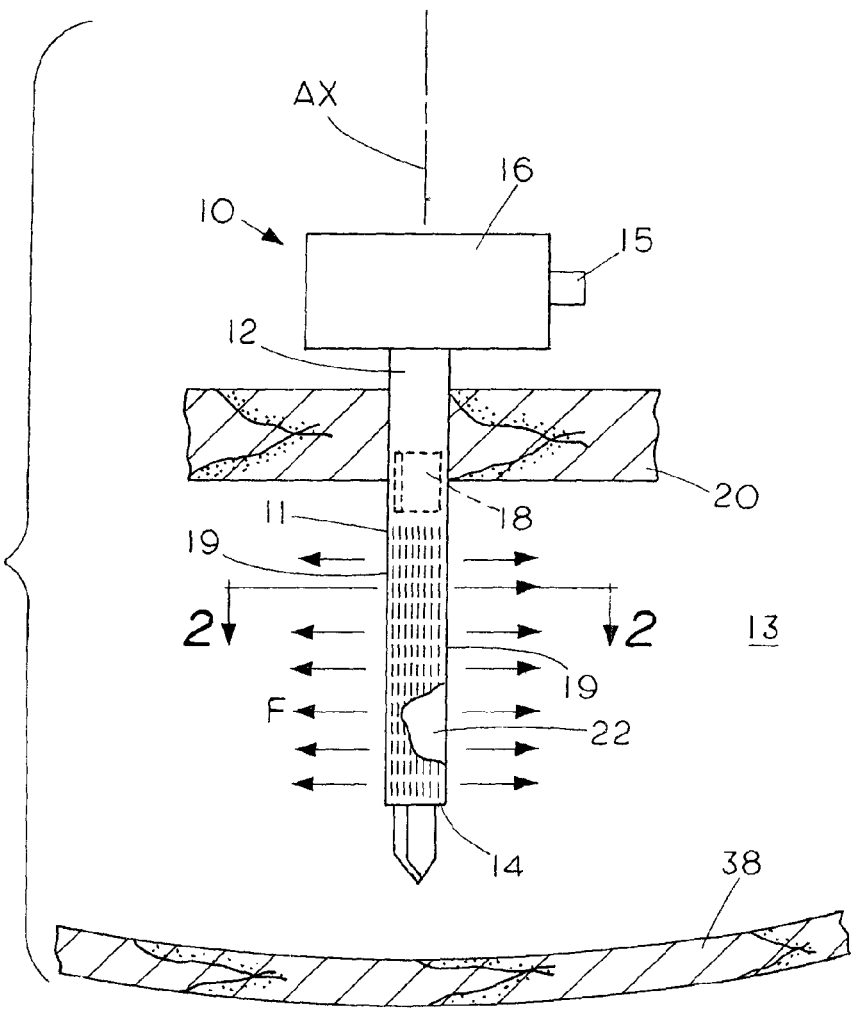
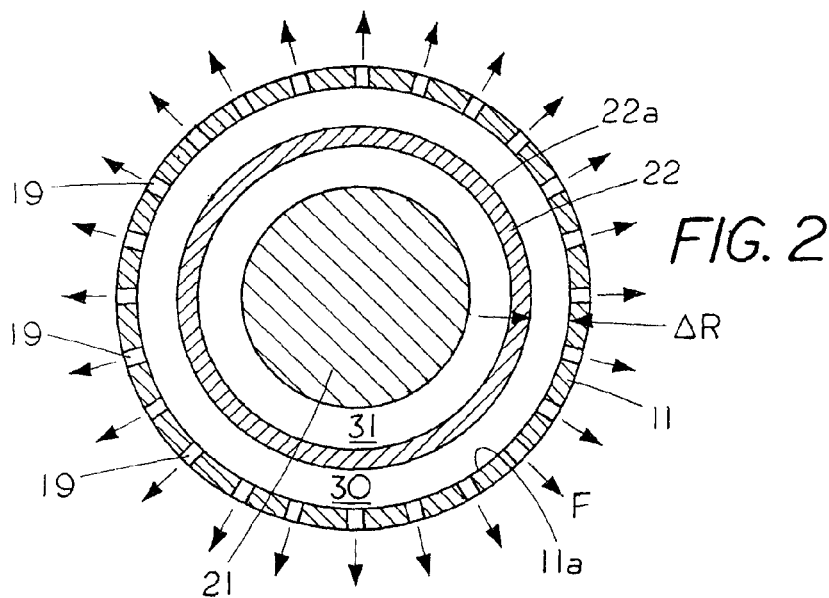

TROCAR SLEEVE

CROSS REFERENCE TO RELATED APPLICATIONS

This application is a continuation of U.S. patent application Ser. No. 14/306,562 filed Jun. 17, 2014 (now U.S. Pat. No. 9,199,046), and a continuation of U.S. patent application Ser. No. 12/658,086 filed Feb. 2, 2010 (now U.S. Pat. No. 9,566,401), which is a continuation of U.S. patent application Ser. No. 11/058,435 filed Feb. 15, 2005 (now U.S. Pat. No. 7,722,558).

FIELD OF THE INVENTION

This invention relates to the field of medical devices, and more specifically to a trocar sleeve for delivery of an insufflation fluid in a non jet-streaming condition regardless of whether instruments are present in the trocar sleeve.

STATEMENT REGARDING FEDERALLY SPONSORED RESEARCH OR DEVELOPMENT

None

REFERENCE TO A MICROFICHE APPENDIX

None

BACKGROUND OF THE INVENTION

A physician can use a trocar device to deliver fluid into a body cavity during specific medical procedures or treatments. The purpose of using such a device is to inflate or distend the body cavity to allow the surgeon (1) exploration of the area in which the surgery will be performed and (2) to provide a view of the site to be treated or observed. Insufflation is used in many common procedures including endoscopic surgical procedures, laparoscopic procedures performed on the abdominal cavity and thoracoscopic procedures performed on the chest cavity.

At the beginning of the procedure, the surgeon cuts an incision to traverse the skin and tissue layers until the body cavity is opened. A Verres need is inserted to start insufflation. A Verres needle may be used, however a trocar can be placed directly without use of a needle to enter the body cavity. An external, pressurized fluid source is connected to the needle. The fluid flows from the proximal end of the needle to a distal end thereof from which the fluid exits and is delivered into the body cavity. This causes the tissue layers to distend, a process known as insufflation. Carbon dioxide gas is commonly used for insufflation and other substances, which may include drugs and anesthetics may be mixed with the carbon dioxide gas and administered simultaneously.

After satisfactory insufflation, the needle is removed and a trocar sleeve may be inserted through the incision and into the body cavity. Trocar sleeves are sized and shaped to pass through the incision and tissue layers of a body so that the sleeve penetrates at least partially into the body cavity. Cameras and/or surgical devices may be inserted into the sleeve to provide the surgeon with a view of the surgical site or to allow the surgeon to treat the area.

My U.S. Pat. No. 6,733,479 discloses, a trocar sleeve with a plurality of apertures that address the problem of the "jet streaming effect" and is hereby incorporated by reference. The "jet streaming effect" is known to damage tissues and/or organs of the body because as the fluid contacts those surfaces, the lining of the body cavity and the surfaces of the organs housed therein undergo severe heat loss. The effect is more fully described in U.S. Pat. No. 6,733,479 and references cited therein. To eliminate or reduce the "jet streaming effect" my prior patent discloses a series of apertures located along the trocar sleeve to effectively distribute the gases at velocities, which are below the threshold of the "jet streaming effect". While the perforated trocar greatly reduces or eliminates the "jet streaming effect" there can be transient conditions when an instrument can periodically obstruct the trocar sleeve and therefore temporarily affect the fluid flow through the trocar sleeve and possibly cause localized regions on the trocar sleeve where the "jet streaming conditions" could occur. For example, a manipulation of an instrument such as surgical device within the trocar sleeve or the insertion of an irregular shaped instrument might block off a substantial portion of the trocar sleeve thereby increasing velocity at other regions of the trocar sleeve until the jet streaming velocity is exceeded. Since this condition is most likely to occur in a localized area and might be only a temporary condition the user might not even know that a "jet streaming condition" is occurring at some of the apertures in the trocar sleeve.

The present invention provides a solution to the problem of transient conditions that can produce localized "jet streaming conditions" by providing a trocar sleeve that does not produce a "jet streaming condition" even though different size and shape instruments are inserted into the trocar sleeve. Furthermore, the instruments can be manipulated in the trocar sleeve without fear of inducing a localized "jet streaming condition". A further embodiment of the invention eliminates the "jet streaming condition" through eliminating of instruments in the trocar sleeve that is used to deliver fluids to a body cavity.

The present invention is a trocar sleeve for insufflating the body cavity without damaging a tissue in the body cavity due to transient flow conditions. More specifically, the invention includes a trocar having a fluid flow chamber that delivers an insufflating fluid at a velocity below a jet streaming velocity whether or not an instrument such as a camera or a surgical device is in the lumen in the trocar sleeve. In one embodiment a double walled trocar sleeve is used to inhibit or prevent the "jet streaming condition" and in another embodiment a blind trocar sleeve is used to inhibit or prevent the "jet streaming condition". In both embodiments, the invention provides a fluid flow condition that is not affected by instruments.

BRIEF SUMMARY OF THE INVENTION

Briefly, one embodiment of the invention comprises a trocar sleeve having an inner wall that isolates an instrument in the trocar sleeve from the insufflation fluid and in another embodiment a blind trocar sleeve is used for insufflations purposes while a conventional trocar sleeve is used for the surgical procedures but not for introducing the insufflating fluid.

BRIEF DESCRIPTION OF THE DRAWINGS

FIG. 1 is a side view of the trocar sleeve;
FIG. 2 is a cross-sectional view of the trocar sleeve taken along lines 2-2 of FIG. 1 illustrating the flow of fluid.

DESCRIPTION OF THE PREFERRED EMBODIMENT

Figure 3:
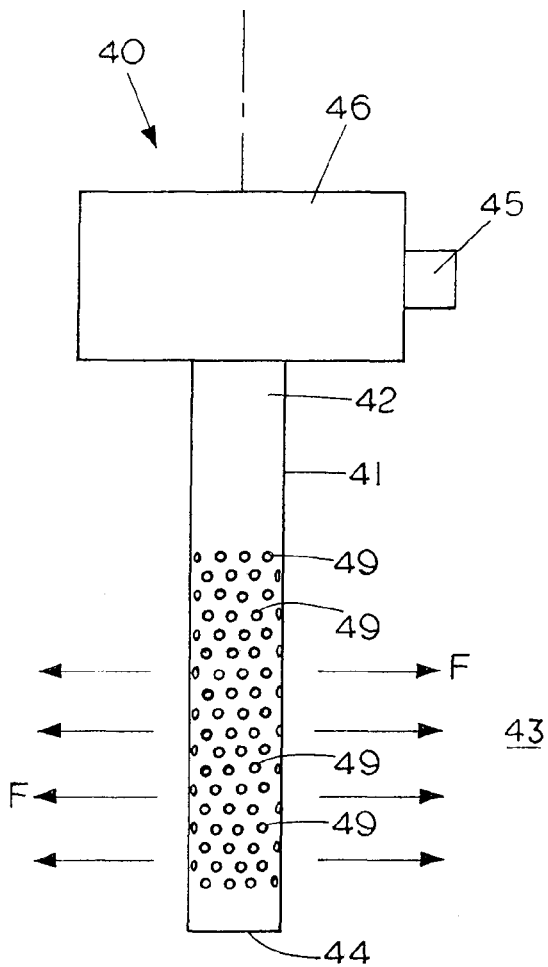
FIG. 3 is side view of the alternate embodiment blind trocar sleeve.

Referring to FIG. 1 and to FIG. 2 the present invention provides a trocar sleeve 10 for insufflating a body cavity while minimizing or eliminating damage to a tissue in the body cavity that can occur proximate the cylindrical member 11 of trocar sleeve 10. Typically, the trocar sleeve is inserted into the body cavity 13 of an animal or human by creating an opening within the body that extends through many layers of tissue 20, which include skin, fat, muscle, and pre-pleural or pre-peritoneal in either the thoracic or abdominal cavities, respectively.

FIG. 1 shows trocar 10 that addresses the problem of transient "jet streaming conditions" that can occur because of partial obstructions within the lumen caused by the insertion of an instruments such as a surgical device through the trocar sleeve 10. Such obstructions, which reduce the diameter of the lumen, can result in high-pressure fluid delivery to the body cavity at localized region proximate the trocar sleeve 10 and thus cause damage to the tissues and/or organs of the body.

FIG. 1 shows trocar sleeve sleeve 10 in a partial cut away view. The trocar sleeve includes a housing 16. Attached to the housing is an inlet port 15. A cylindrical member or tube 11 is attached to the housing and is formed about a central longitudinal axis $A_x$ of the trocar sleeve. The cylindrical member 11 has a proximal end 12 and spaced distally therein is a distal end 14. A spaced plurality of apertures 19 is defined within the exterior of the body surface of the cylindrical member 11. The plurality of apertures 19 are regularly spaced from one another and extend at least partially from the distal end 14 toward the proximal end 12 of the trocar sleeve. The plurality of apertures 19 can extend the entire length of the trocar sleeve if so desired, or for any desired length along the trocar sleeve. It is anticipated that although the respective apertures may extend along the entire length of the trocar sleeve if so desired, the apertures will preferably be spaced from the proximal ends.

Within the cylindrical member 11 and attached to the housing 16 is a cylindrical member or tube 22 having a sidewall 22a which is impervious or substantially impervious to fluid flow therethrough.

FIG. 2 shows a cross section view revealing the outer elongated tube or cylindrical member 11 having the apertures 19 therein. Located concentrically within cylindrical member 11 is a further elongated tube or cylindrical member 22 having the sidewall 22a impervious to fluid flow with sidewall 22a spaced from inner sidewall 11a of tube 11 to form an annular chamber 30 for fluid to flow therethrough. Positioned within lumen 31 of cylindrical member 22 is the instrument comprising trocar 21, which is shown occupying a central portion of the lumen 31. In use, the trocar 21 might occupy more or less of the lumen 31. The lumen 31 is used for manipulating the instruments and is isolated from the annular chamber 30. That is, the lumen 31 is not used to deliver the insufflation gas to the patient any consequently manipulation of the surgical device 21 within the lumen 31 does not have any effect on the flow through the annular chamber 30 and hence through the radial apertures 19. Thus, once a "non jet streaming condition" is established at apertures 19 any changes in the position of the instrument or the type of instrument in the lumen 31 will not have any effect on the velocity of the fluids escaping from the apertures since the flow through the apertures is isolated from the instruments located in the lumen 31 of the trocar sleeve 10. Thus, the present invention is well suited for those applications where the instruments inserted through the trocar sleeve are of different size or shape since the size, shape or the position of the instrument does not effect the flow through the trocar sleeve 11. In addition, any repositioning of the instruments in the lumen 31 will not have any effect on flow conditions through the trocar sleeve since the fluid flow is independent of conditions in lumen 31.

FIG. 2 illustrates the radial fluid flow through trocar sleeve 10. An insufflating fluid,"F", which may be gas, liquid containing drugs, anesthetic or other substances placed or mixed within a pharmaceutically acceptable carrier or any combination thereof. The fluid "F" is delivered under pressure from an external source via inlet port 15, travels through the annular fluid flow chamber 30 and is discharged at below a "jet streaming velocity" through the plurality of apertures 19 as indicated by the arrows. Thus regardless of whether an instrument is present in lumen 31 or whether an instrument is manipulated in lumen 31 it will not have an effect on the fluid conditions through the apertures or fluid ports 19.

FIG. 3 illustrate an alternate embodiment 40 of the invention wherein a "non-jet streaming condition" can also be maintained. Specifically, the embodiment 40 includes a housing 46 and attached to the housing is an inlet port 45 and a tube or cylindrical member 41 having a proximal end 42 and spaced therefrom a distal end 44. Along the exterior surface of the cylindrical member 41 is a plurality of fluid ports or apertures 49. As can be seen in FIG. 3 the arrows indicate an insufflation fluid is directed radially outward from the apertures 49 and is maintained at a non-jet streaming velocity by control pressure conditions within cylindrical member 41. Thus by having member 41 having a chamber 47 therein with 41 apertures sufficiently small to preclude insertions of instruments therethrough one ensures that instruments will not be inserted into trocar sleeve 40 and adversely affect the established non jet streaming conditions.

Figure 3A:
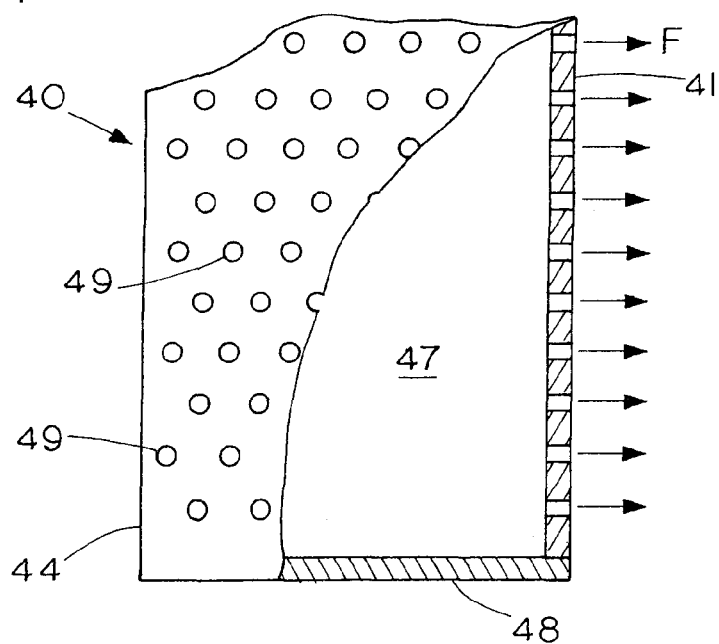
FIG. 3A is a cut away and enlarged view of a portion of the alternative embodiment the blind trocar sleeve of FIG. 3.

FIG. 3A is a partial cut away view of the cylindrical member 41 revealing an end member 48 blocking the end of cylindrical member 41 to provide a closed end of trocar sleeve 40 to prevent extension of an instrument or other device into plenum chamber 47. This allows one to establish fluid flow conditions in plenum chamber 47 that produce fluid velocities through apertures 49 that are below a "jet streaming velocity" and will remain at below a "jet streaming velocity" since no instruments or other devices are inserted into the plenum chamber 47 to affect the velocity of the fluid discharged through apertures 49.

FIG. 3 and FIG. 3A show insufflating fluid flow delivered from within the blind trocar sleeve 40. In operation fluid flows from an external source under pressure through the inlet port 45, is carried through the cylindrical member 41 and flows into plenum chamber 47 and through the plurality of apertures 49 into the body cavity 43. In the embodiment of FIGS. 3 and 3A because the trocar sleeve is blind no instrument can be inserted therethrough. Since no instrument can be inserted therein one need not be concerned with the size, shape or type of instrument as well as the position of the instrument affecting the fluid flow conditions proximate the cylindrical member 41. Thus once the "non-jet streaming condition" is established in trocar sleeve 40 one can be assured that the non jet streaming condition can be maintained proximate the trocar sleeve 40. However, if a surgical instrument needs to be inserted into the body cavity it can be inserted into a companion or separate trocar sleeve that does not contain the insufflation gas. The end 48 may or may not have apertures 49 to allow fluid flow as well as from the side wall.

Thus, the invention includes the method of insufflating a body cavity without damaging a tissue in the body cavity that can occur during transient conditions within the trocar sleeve by directing a fluid flow from a first chamber in a trocar sleeve through apertures in the trocar sleeve at a velocity less than a jet streaming velocity while inserting or manipulating an instrument in a further chamber that is isolated from the first chamber to prevent the instrument therein from affecting the flow of fluid from the first chamber to thereby maintain the velocity of the fluid at less than the jet streaming velocity.

I claim:

1. A trocar sleeve, comprising:
   a housing;
   an inlet port connected to the housing and adapted to receive an insufflation gas;
   a first member connected to the housing, the first member having a first passage therein that is not coupled to the inlet port, the first passage adapted to receive an instrument during a surgical procedure; and
   a second member connected to the housing wherein the second member is further coupled to the inlet port and includes a distal end for insertion into a body cavity during a surgical procedure, wherein the outer wall of the first member and the inner wall of the second member form a second circumferential passage extending proximal from the inlet port to the distal end of the second member and adapted to receive at least some of the insufflation gas;
   wherein the second member further comprises a plurality of apertures in the outer wall of the second member, the plurality of apertures adapted to discharge at least some of the insufflation gas received in the second circumferential passage into a body cavity during a surgical procedure.

2. The trocar sleeve of claim 1 wherein the distal end has an open end.

3. The trocar sleeve of claim 1 wherein the distal end has a closed end.

4. The trocar sleeve of claim 1, wherein the second member is coaxial with the first member.

5. The trocar sleeve of claim 1, wherein the first member comprises a cylindrical tube.

6. The trocar sleeve of claim 1, wherein the second member comprises a cylindrical tube.

7. The trocar sleeve of claim 1, wherein the sidewall of the first member is impervious to fluid flow therethrough and the second circumferential passage is an annular passage.

8. The trocar sleeve of claim 1, wherein the plurality of apertures is regularly spaced from one another.

9. The trocar sleeve of claim 1, wherein the plurality of apertures is randomly spaced from one another.

10. The trocar sleeve of claim 1, wherein the second member is spaced radially outward from the first member.

11. The trocar sleeve of claim 1, wherein the instrument comprises a trocar.

12. The trocar sleeve of claim 1, wherein the instrument comprises a surgical device.

13. The trocar sleeve of claim 1, wherein the instrument comprises a camera.

14. The trocar sleeve of claim 1, wherein the inlet port does not supply any gas to the first passage.

15. The trocar sleeve of claim 1, wherein inlet port is adapted to receive carbon dioxide insufflation gas.

16. The trocar sleeve of claim 1, wherein the first passage is not adapted to deliver gas from an insufflator to a patient while gas from the insufflator is flowing through the second passage.

17. The trocar sleeve of claim 1, wherein the second member is coaxial with the first member along an entire length of the first member.

18. The trocar sleeve of claim 1, wherein the plurality of apertures has a cross sectional fluid discharge area adapted to maintain a velocity of insufflation gas discharging from the plurality of apertures in a non jet streaming condition.

* * * * *